United States Patent [19]

Stanzak

[11] Patent Number: 5,057,425
[45] Date of Patent: Oct. 15, 1991

[54] PICROMYCIN RESISTANCE-CONFERRING GENE, DESIGNATED PICA, FOR USE IN STREPTOMYCES AND OTHER ORGANISMS

[75] Inventor: Richard K. Stanzak, Poland, Ind.

[73] Assignee: Eli Lilly and Company, Indianapolis, Ind.

[21] Appl. No.: 226,360

[22] Filed: Jul. 29, 1988

[51] Int. Cl.$^5$ .............................. C12N 1/21; C12N 15; C12N 52; C12N 15/70; C12N 15/74
[52] U.S. Cl. ........................... 435/252.3; 435/69.1; 435/71.1; 435/34; 435/91; 435/169; 435/172.1; 435/172.3; 435/320.1; 435/886; 536/27; 935/6; 935/9; 935/22; 935/29; 935/33; 935/38; 935/39; 935/59; 935/66; 935/72; 935/75
[58] Field of Search ................. 536/27; 435/69.1, 71.1, 435/34, 91, 169, 172.1, 172.3, 252.3, 320.1, 886; 935/6, 9, 22, 29, 33, 38, 39, 59, 66, 72, 75

[56] References Cited

U.S. PATENT DOCUMENTS 4,680,265  7/9187   Birmingham et al. ............. 435/69.1
4,704,362  11/1987  Itakura et al. .................... 435/253.3
4,753,880  6/1988   Schaus et al. .................... 435/172.3

OTHER PUBLICATIONS

Benveniste and Davies, 1973, Proc. Natl. Acad. Sci. USA 70(8): 2276-2280.
Thompson et al., 1980, Nature 286:525-527.
Fujisawa and Weisblum, 1981, J. Bacteriol. 146(2): 621-631.
Thompson et al., 1982, Bacteriol. 151(2):668-677.
Thompson et al., 1982, J. Bacteriol. 151(2):678-685.
Thompson et al., 1982, Gene 20:51-62.
Murakami et al., 1983, J. Antibiotics 36(10):1305-1311.
Tohyama et al., 1984, J. Antibiotics 3712):1736-1737.
Nakano et al., 1984, J. Bacteriol. 157(1):79-83.
Bibb et al., 1985, Mol. Gen. Genet. 199:26-36.
Ohnuki et al., 1985, J. Bacteriol. 161(3):1010-1016.
Distler et al., 1985, FEMS Microbiology Letters 30:151-154.
Vara et al., 1985, Gene 33:197-206.
Brimingham et al., 1984, Abstracts of the ASM Conference on Genetics and Molecular Biology of Industrial Microorganisms, Bloomington, IN, Abstract No. 220.

*Primary Examiner*—Richard A. Schwartz
*Assistant Examiner*—Richard C. Peet
*Attorney, Agent, or Firm*—Douglas K. Norman; Leroy Whitaker

[57] ABSTRACT

A novel gene conferring resistance to picromycin in Streptomyces and related organisms was cloned from a genomic library of *Streptomyces felleus* DNA. The novel picromycin resistance-conferring gene can be isolated on an ~2.8 kb PvuII fragment by subcloning the restriction fragment from plasmid pOJ321. This PvuII fragment contains all of the information required for the expression of the picromycin resistant phenotype in Streptomyces. Methods for inducing resistance, as well as vectors and transformants containing the novel picromycin resistance gene, are provided.

31 Claims, 5 Drawing Sheets

Restriction Site and Function Map of Plasmid pOJ321
(~9.9 kb)

Restriction Site and Function Map of Plasmids pFJ370 and pFJ371 pFJ370 pFJ371

Restriction Site and Function Map of Plasmids pFJ372 and pFJ373 pFJ372 pFJ373

Restriction Site and Function Map of Plasmids pFJ374 and pFJ375 pFJ374 pFJ375

Restriction Site and Function Map of Plasmids pFJ376 and pFJ377 pFJ376 pFJ377

PICROMYCIN RESISTANCE-CONFERRING GENE, DESIGNATED PICA, FOR USE IN STREPTOMYCES AND OTHER ORGANISMS

SUMMARY OF THE INVENTION

The present invention comprises a novel picromycin resistance-conferring gene, designated picA, a method for inducing the picA gene, recombinant DNA cloning vectors that comprise the novel gene, and transformants containing the picromycin resistance-conferring vectors. Streptomyces felleus (NRRL 2251) produces picromycin, a macrolide antibiotic consisting of a 14-member cyclic lactone and one sugar residue. The antibiotic activity of picromycin, like that of other macrolides, is due to inhibition of protein synthesis by a mechanism that involves the binding of picromycin to the ribosome.

The present invention provides picromycin resistance-conferring cloning vectors for use in Streptomyces and other host cells. The development and exploitation of recombinant DNA technology in Streptomyces depends upon the availability of selectable genetic markers on suitable cloning vectors. See Nakanishi (1986) Plasmid 15:217–229. This development has been somewhat retarded by the low number of selectable markers presently available for use in Streptomyces. The present invention is useful and especially important in that it expands the number of selectable markers suitable for such use.

The vectors of the present invention are particularly useful, because the vectors are small, versatile, and can be transformed and selected in a variety of picromycin-sensitive Streptomyces cells. Streptomyces provides over half of the clinically important antibiotics and thus is a commercially significant group. The present invention provides new and useful cloning systems and vectors for this industrially important group and allows for the cloning of genes both for increasing the yields of known antibiotics and also for producing new antibiotics and antibiotic derivatives.

The present invention further provides vectors that enable identification of Streptomyces transformants. After the addition of non-selectable DNA to a vector of the present invention, the modified vector can be transformed into Streptomyces and transformants identified by their picromycin-resistant phenotype. Because transformation is a relatively low frequency event, such a functional test is a practical necessity for determining which cell(s), of among the millions of cells, has acquired the transforming DNA.

For purposes of the present invention, as disclosed and claimed herein, the following terms are defined below.

Am$^R$—the apramycin-resistant phenotype or gene conferring same.

Ap$^R$—the ampicillin-resistant phenotype or gene conferring same.

Car—carbomycin.
Ery—erythromycin.
Linc—lincomycin.
mel—the tyrosinase gene.
Pc—picromycin.
picA—a picromycin resistance-conferring gene.
Phasmid—a recombinant DNA vector that may act as a phage or as a plasmid.
Recombinant DNA Cloning Vector—any autonomously replicating or integrating agent, including, but not limited to, plasmids, comprising a DNA molecule to which one or more additional DNA segments can be or have been added.

Restriction Fragment—any linear DNA molecule generated by the action of one or more restriction enzymes.

Ros—rosaromycin.

Sensitive Host Cell—a host cell that cannot grow in the presence of a given antibiotic without a DNA segment that provides resistance thereto.

Spi—spiramycin.

Tc$^R$—the tetracycline-resistant phenotype or gene conferring same.

Transformant—a recipient host cell that has undergone transformation.

Transformation—the introduction of DNA into a recipient host cell that changes the genotype and results in a change in the recipient cell.

tsr$^R$—the thiostrepton-resistant phenotype or gene conferring same.

Tyl—tylosin.

DETAILED DESCRIPTION OF THE INVENTION

The present invention is a recombinant DNA cloning vector which comprises a) a DNA sequence selected from the group consisting of an origin of replication and an integration sequence, and b) a picromycin resistance gene that confers resistance to antibiotic picromycin, subject to the limitation that said origin of replication and integration sequence are functional in Streptomyces and Nocardia.

Figure 2:
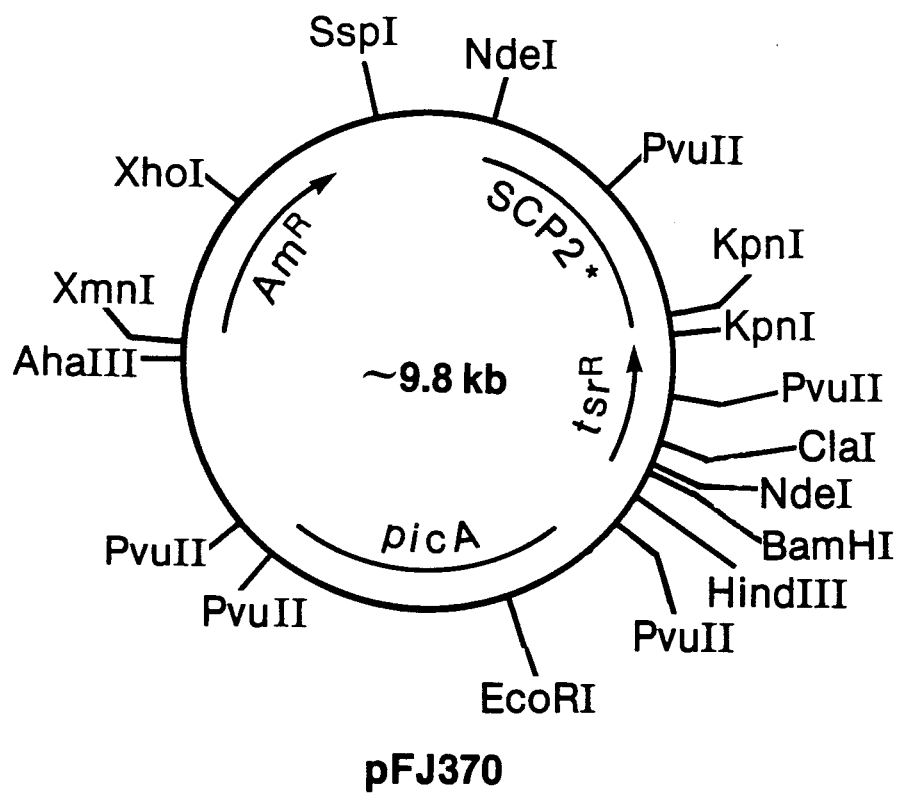
FIG. 2—the restriction site and function maps of plasmids pFJ370 and pFJ371.
Figure 2:
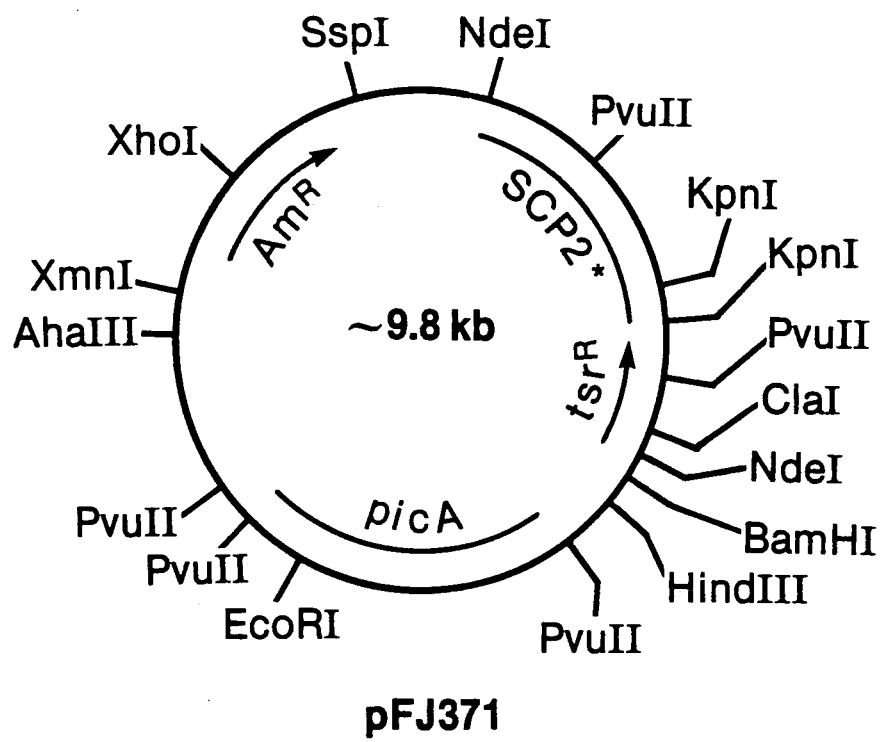

The present invention can be constructed by ligating the picromycin resistance gene (picA) containing the ~2.8 kb PvuII fragment of plasmid pOJ321 into partially PvuII-digested plasmid pOJ160 to form plasmids pFJ370 and pFJ371, which differ only in respect to the orientation of the picA gene. Restriction site and function maps of plasmids pFJ370 and pFJ371 are presented in FIG. 2 of the accompanying drawings. Plasmid pOJ321 can be obtained from E. coli K12 JM109/pOJ321, a strain deposited and part of the permanent stock culture collection of the Northern Regional Research Laboratory (NRRL), Agricultural Research Service, 1815 North University Street, U.S. Department of Agriculture, Peoria, IL 61604. It is available to the public as a source and stock reservoir of the plasmid under the accession number NRRL B-18389. Plasmid pOJ160 can be isolated from E. coli K12 JM109/pOJ160, also available from the NRRL under the accession number NRRL B-18088.

Skilled artisans will readily recognize that for certain purposes and under certain conditions it is more convenient to propagate cloning vectors in *E. coli* than in Streptomyces and related organisms. Consequently, the vectors of the present invention can be modified to be bifunctional shuttle vectors operable in both *E. coli* and Streptomyces. This is done by providing an appropriate *E. coli* origin of replication and selectable sequence to a Streptomyces picromycin resistance-conferring vector. Thus, the present vectors which additionally comprise a) an *E. coli* origin of replication, and b) a DNA sequence that confers a selectable phenotype in *E. coli*.

Figure 1:
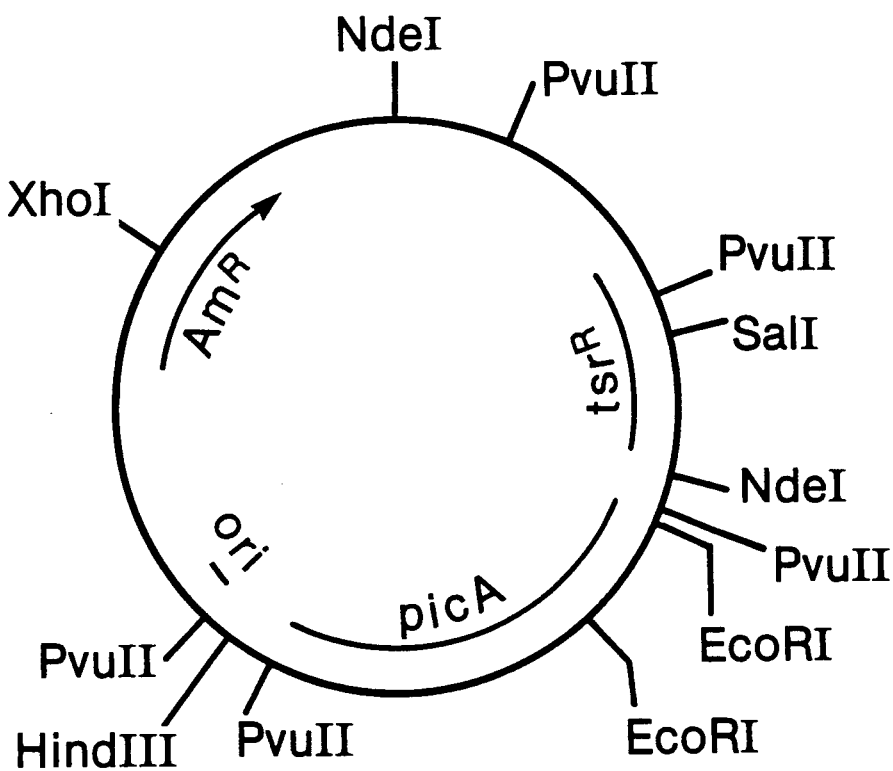
FIG. 1—the restriction site and function map of plasmids pOJ321. For the purpose of this disclosure, the Figures are not drawn exactly to scale.

Plasmid pOJ321 is an illustrative bifunctional shuttle vector that contains picA, a Streptomyces replicon, an *E. coli* replicon, and an apramycin resistance gene that confers a selectable phenotype in both Streptomyces and *E. coli*. It can be obtained from *E. coli* K12 JM109/pOJ321 which has been deposited at NRRL as described above. A restriction site and function map of plasmid pOJ321 is presented in FIG. 1 of the accompanying drawings.

The present vectors comprise a novel picromycin resistance gene that was isolated from a known strain of *Streptomyces felleus* (NRRL 2251). The present gene confers resistance to the macrolide antibiotic picromycin and, in some cases, simultaneously to other antibiotics as well. Such cross resistance for certain antibiotic resistance genes is a known phenomenon reported by several authors, including Fujisawa and Weisblum, *J. Bacteriology* 146: 621 (1981).

Figure 3:
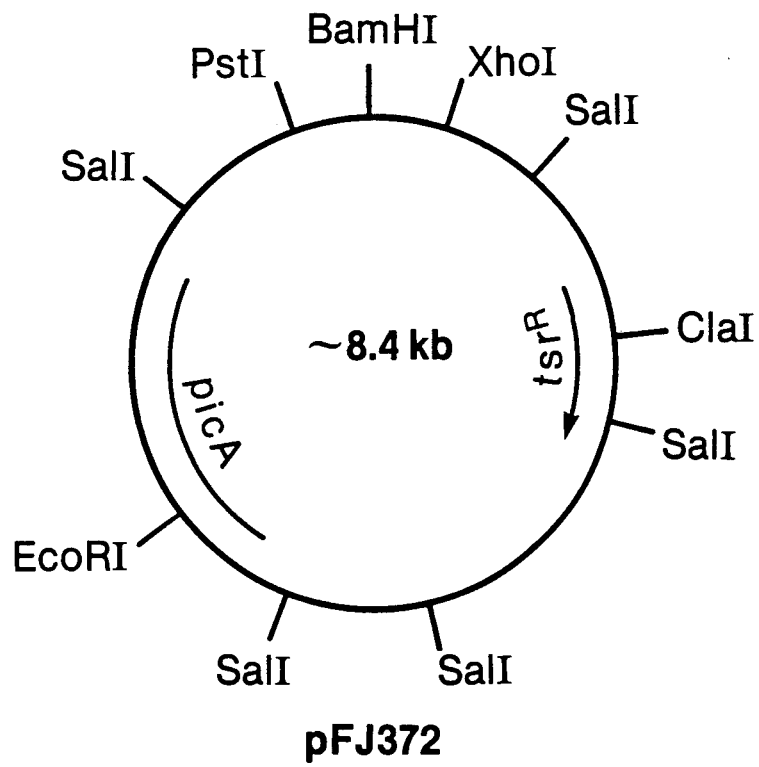
FIG. 3—the restriction site and function maps of plasmids pFJ372 and pFJ373.
Figure 3:
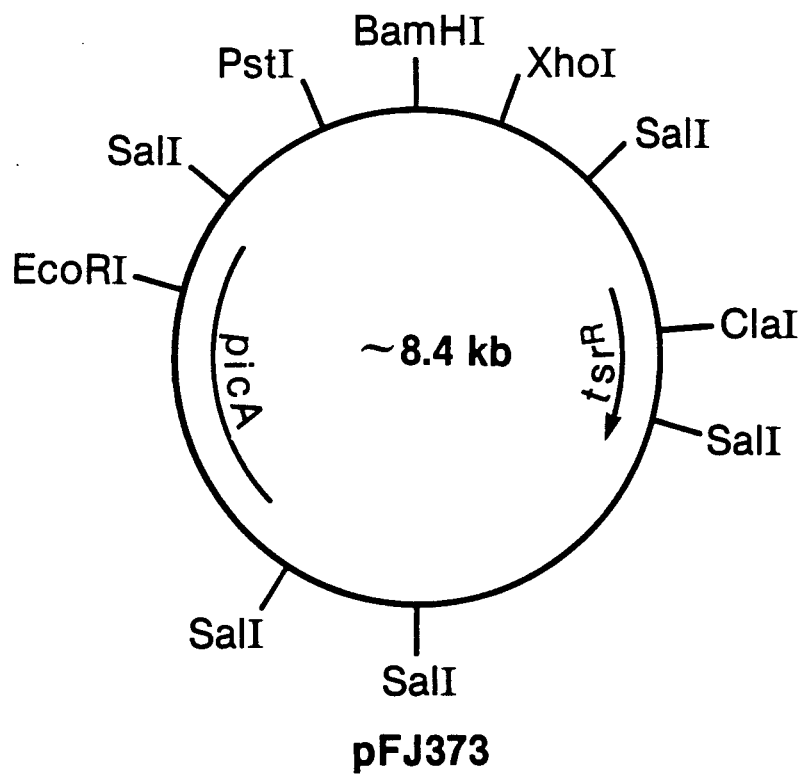

The ~2.8 kb picA gene-containing restriction fragment can also be cloned into conventional Streptomyces vectors which contain only a Streptomyces replicon. For example, the ~2.8 kb PvuII fragment can be ligated into the single BglII site of plasmid pIJ702 after the 5' overhang of the BglII site is first filled-in using T4 DNA polymerase. This reaction forms plasmids pFJ372 and pFJ373, which differ only in the orientation of the picA fragment. These plasmids, when transformed into Streptomyces spp, can confer picromycin resistance to a picromycin sensitive host. Plasmid pIJ702 can be obtained from *Streptomyces lividans*/pIJ702, a strain deposited and made part of the permanent stock culture collection of the American Type Culture Collection (ATCC), Rockville, Md., 20852. It is available to the public as a source and stock reservoir of the plasmid under the accession number ATCC 39155. Restriction site and function maps of plasmids pFJ372 and pFJ373 are presented in FIG. 3 of the accompanying drawings.

The ~2.8 kb picA gene-containing restriction fragment can further be used to confer picromycin resistance to a sensitive host via homologous recombination and integration into the host's genome. For example, *Streptomyces griseofuscus* chromosomal DNA (ATCC 23916) can be partially digested with MboI restriction enzyme and then the 5' overhangs filled-in using T4 DNA Polymerase. This DNA is then ligated into EcoRI cut, filled-in plasmid pBR322 (BRL) and transformed into *E. coli* 294 cells, selecting for tetracycline resistance. The resultant plasmids are then partially digested with PvuII restriction enzyme and the ~2.8 kb picA gene-containing fragment from pOJ321 are then ligated into the PvuII sites. The ligated plasmids are then transformed into *E. coli* and selected on tetracycline plates. The transformants are pooled and the plasmids, which differ only in the orientation of the picA fragment, are designated pFJ374 and pFJ375. When back-transformed into *Streptomyces griseofuscus*, these plasmids cannot autonomously replicate because they contain no Streptomyces replicon. Therefore the only resistant colonies which arise are those which grow from cells in which a homologous recombination and subsequent integration event has occurred. Restriction site and function maps of plasmids pFJ374 and pFJ375 are presented in FIG. 4 of the accompanying drawings. It should be noted that even when the picA gene is carried on a plasmid which contains a Streptomyces replicon, a low, but still detectable, number of integration events may still occur in any culture. Therefore, an autonomously replicating vector might also "integrate" albeit at a low frequency.

Figure 5:
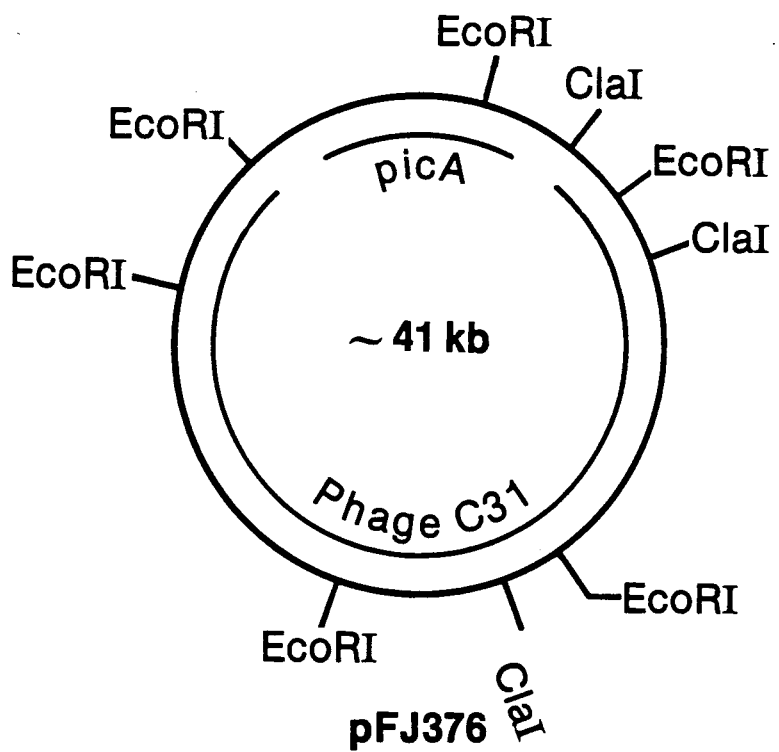
FIG. 5—the restriction site and function maps of phages pFJ376 and pFJ377.
Figure 5:
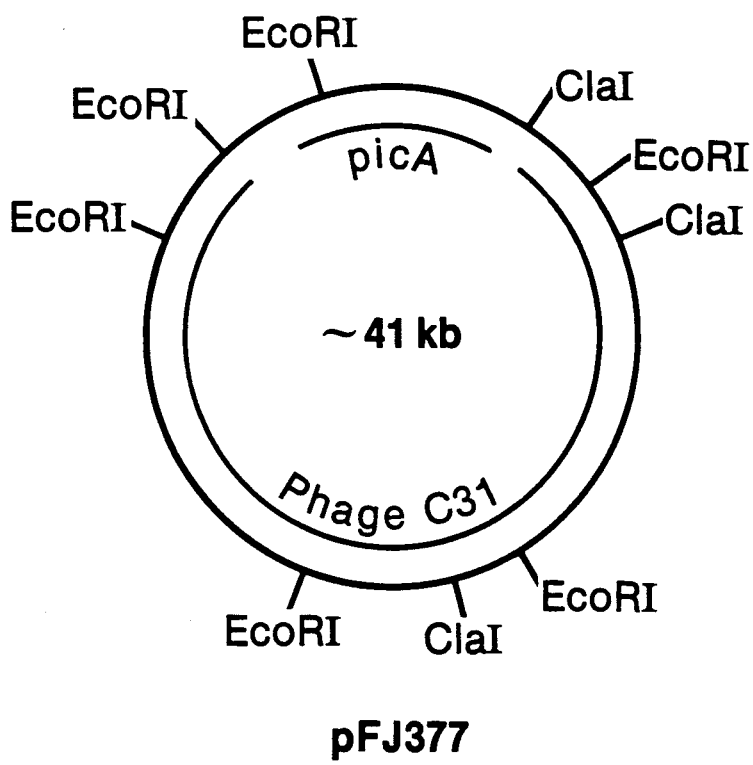

The picA gene can also be used to construct illustrative vectors other than plasmids. For example, phage φC31 is a well known Streptomyces phage that is an excellent starting material for constructing certain other integrative vectors. A derivative of phage φC31, phasmid pKC331, is especially preferred for constructing such integrating vectors and can be obtained from *E. coli* K12 BE447/pKC331, a strain deposited and made part of the permanent stock culture collection of the aforementioned Northern Regional Research Laboratory under the accession number NRRL B-15828. Ligation of the ~37 Kb PstI restriction fragment of phasmid pKC331 to the ~2.8 kb picromycin resistance-conferring PvuII restriction fragment of plasmid pOJ321, (after the 3' overhang of the PstI fragment has been chewed back using T4 DNA polymerase), results in the derivative phages pFJ376 and pFJ377, which differ only in the orientation of the picA gene. These phages are integrative vectors which confer picromycin-resistance to Streptomyces and thus further exemplify the present invention. Restriction site and function maps of phages pFJ376 and pFJ377 are presented in FIG. 5 of the accompanying drawings.

It will be understood that the picA gene-containing restriction fragments are not limited to a particular vector or a position on a cloning vector. For example, the picromycin resistance gene can be subcloned into other known vectors such as the pSCP103-derived plasmids (Lydiate et al., 1985, Gene 35:223), the pFJ103-derived plasmids (Richardson et al., 1982, Gene 20:451, and pHJL400 (Hershberger et al. 1986, Plasmid 15:199-209), to name a few. Those skilled in the art understand or can readily determine which vector is desirable for a specific purpose and which sites on a vector are advantageous for the ligation or insertion of a particular picromycin resistance gene-containing restriction fragment. In addition, molecular linkers can be provided, thereby creating specific sites for DNA subcloning, or the fragment can be modified by adding, eliminating or substituting certain nucleotides to alter characteristics and provide a variety of restriction sites for ligation of DNA. Those skilled in the art understand nucleotide chemistry and the genetic code and thus which DNA modifications are desirable for a specific purpose.

Although illustrative plasmid pOJ321 comprises the SCP2* Streptomyces replicon derived from a cosmid constructed from pHJL400, a variety of other Streptomyces replicons can also be substituted to construct similar vectors. Table.1 is an illustrative, but not comprehensive, listing of Streptomyces plasmids from which additional, functional Streptomyces replicons can be obtained. Those skilled in the art recognize that all or part of the plasmids may be used to construct vectors exemplifying the present invention so long as the replicon function is not disrupted. The plasmid-containing host an depository accession number are also listed in Table 1.

TABLE I

| Streptomyces Plasmids | | |
|---|---|---|
| Plasmid | Host | Accession Number |
| SCP2 | Streptomyces coelicolor A3(2) | NRRL 15042 |
| pEL7 | Streptomyces ambofaciens | NRRL 12523 |
| SLP1 | Streptomyces lividans | NCIB[1] 11417 |
| pNM100 | Streptomyces virginiae | NRRL 15156 |
| pEL103 | Streptomyces granuloruber A39912.13/pEL103 | NRRL 12549 |
| pIJ702 | Streptomyces lividans | ATCC[2] 39155 |

Other replicons such as SLP1.2 (Horinouchi et al., 1985, J. Bacteriol. 162:406), pSRC1-b (Shindoh et al., 1984, J. Antibiot. 37:512), pSL1 (Nakano et al., 1982, FEMS Microbiol. Lett. 13:279) and pSF765 (Murakami et al., 1983, J. Antibiot. 36:429) may also be used and are therefore within the scope of the present invention.
[1]National Collection of Industrial Bacteria (NCIB), Torry Research Station, Post Office Box 31, 135 Abbey Road, Aberdeen AB98DG, Scotland, United Kingdom
[2]American Type Culture Collection (ATCC), 12301 Parklawn Drive, Rockville, Maryland 20582, United States of America The vectors of the present invention comprise a Streptomyces replicon, a picromycin resistance-conferring restriction fragment and optionally, an *E. coli* replicon and selectable sequence. Because amplification and manipulation of plasmids is done faster and more efficiently in *E. coli* than in Streptomyces, the presence of an *E. coli* replicon is advantageous and adds to the general utility of the present illustrative vectors. In fact, the wealth of genetic and biochemical information about *E. coli* makes it a convenient host cell for purposes of the present invention. However, the invention is not limited to any one species or strain but can be used with any organism where the *E. coli* replicon is functional. Since the presence of a particular *E. coli* replicon is not a critical component of the present vectors, the substitution of functional replicon-containing and, if desired, antibiotic resistance-conferring restriction fragments from *E. coli* plasmids such as, for example, pCZ101 (Schoner et al., 1984, *Proc. Natl. Acad. Sci. USA* 81:5403), pACYC184, pBR325, pBR328 and the like is within the scope of the present invention. A number of other host cells are also apparent to those skilled in the art.

The recombinant DNA cloning vectors of the present invention are also not limited for use in a single species or strain of Streptomyces. To the contrary, the vectors are broadly applicable and can be used with macrolide-sensitive host cells of many Streptomyces taxa, particularly restrictionless strains of economically important taxa that produce antibiotics such as aminoglycoside, macrolide, β-lactam, polyether and glycopeptide antibiotics. Such restrictionless strains are readily selected and isolated from Streptomyces taxa by conventional procedures well known in the art (Lomovskaya et al., 1980, *Microbiology Reviews* 44:206). Host cells of restrictionless s-trains lack restriction enzymes and, therefore, do not cut or degrade plasmid DNA upon transformation. For purposes of the present application, host cells containing restriction enzymes that do not cut any of the restriction sites cf the present vectors are also considered restrictionless.

The picA gene can be used to transform a variety of picromycin-sensitive organisms to picromycin resistance. In organisms naturally sensitive to macrolide antibiotics, including picromycin, the picA gene can be used as a genetic marker. In organisms that produce one or more macrolide antibiotics yet are sensitive to low levels of macrolide antibiotic, the vectors of the present invention can be used to increase or augment the organism's natural resistance. In addition, the picA gene also confers resistance to a wide variety of other antibiotics, such as spiramycin, rosaromycin, lincomycin, erythromycin, carbomycin and tylosin. Preferred host cells of restrictionless strains of picromycin-sensitive Streptomyces taxa, and in which the present vectors may be transformed, include restrictionless cells of, for example: *Streptomyces coelicolor, S. granuloruber, S. roseosporus, S. acrimycins, S. glaucescens, S. parvilin, S. pristinaespiralis, S. violaceoruber, S. vinaceus, S. espinosus, S. azureus, S. griseofuscus, S. fradiae* and *S. toyocaensis.*

The following Tables present a representative sampling of various other antibiotic-producing organisms in which the picA gene can also be used.

TABLE II

| Aminocyclitol Antibiotic-Producing Organisms | |
|---|---|
| Organism | Antibiotic |
| Bacillus various species | various aminocyclitols |
| Micromonospora various species | gentamycins |
| Saccharopolyspora various species | various aminocyclitols |
| Streptomyces | |
| *albogriseolus* | neomycins |
| *albus* var. *metamycinus* | metamycin |
| *aquacanus* | N-methyl hygromycin B |
| *atrofaciens* | hygromycins |
| *bikiniensis* | streptomycin |
| *bluensis* var. *bluensis* | bluensomycin |
| *canus* | ribosyl paromamine |
| *catenulae* | catenulin |
| *chrestomyceticus* | aminosidine |
| *crystallinus* | hygromycin A |
| *erythrochromogenes* var. *narutoensis* | streptomycin |
| *eurocidicus* | A16316-C |
| *fradiae* | hybrimycins and neomycins |
| *fradiae* var. *italicus* | aminosidine |
| *galbus* | streptomycin |
| *griseus* | streptomycin |
| *griseoflavus* | MA 1267 |
| *hofuensis* | seldomycin complex |
| *hygroscopicus* | hygromycins, leucanicidin, and Hygrolidin |
| *hygroscopicus* forma *glebosus* | glebomycin |
| *hygroscopicus* var. *limoneus* | validamycins |
| *hygroscopicus* var. *sagamiensis* | spectinomycin |
| *kanamyceticus* | kanamycin A and B |
| *kasugaensis* | kasugamycins |
| *kasugaspinus* | kasugamycins |
| *lavendulae* | neomycin |
| *lividus* | lividomycins |
| *mashuensis* | streptomycin |
| *microsporeus* | SF-767 |
| *netropsis* | LL-AM31 |
| *noboritoensis* | hygromycins |
| *olivaceus* | streptomycin |
| *olivoreticuli* var. *cellulophilus* | destomycin A |
| *poolensis* | streptomycin |
| *rameus* | streptomycin |
| *ribosidificus* | SF733 |
| *rimofaciens* | destomycin A |
| *rimosus* forma *paromomycinus* | paromomycins and catenulin |
| *spectabilis* | spectinomycin |
| *tenebrarius* | tobramycin and apramycin |
| *Streptoverticillium flavopersicus* | spectinomycin |

TABLE III

| Ansamycin Antibiotic-Producing Organisms | |
|---|---|
| Organism | Antibiotic |
| Micromonospora various species | various ansamycins |
| Nocardia mediterranei | rifamycin |
| Streptomyces | |
| *collinus* | ansatrienes and napthomycins |

TABLE III-continued

Ansamycin Antibiotic-Producing Organisms

| Organism | Antibiotic |
|---|---|
| diastochromogenes | ansatrienes and napthomycins |
| galbus subsp. griseosporeus | napthomycin B |
| hygroscopicus | herbimycin |
| hygroscopicus var. geldanus var. nova | geldamycin |
| nigellus | 21-hydroxy-25-demethyl 25-methylthioproto-streptovaricin |
| rishiriensis | mycotrienes |
| sp. E/784 | actamycin and mycotrienes |
| sp. E88 | mycotrienes |
| spectabilis | streptovaricins |
| tolypophorous | tolypomycin |

TABLE IV

Anthracycline and Quinone Antibiotic-Producing Organisms

| Organism | Antibiotic |
|---|---|
| Streptomyces | |
| caespitosus | mitomycins A, B, and C |
| coelicolor | actinorhodin |
| coeruleorubidicus | daunomycin |
| cyaneus | ditrisarubicin |
| flavogriseus | cyanocycline A |
| galilaeus | aclacinomycin A, auramycins, and sulfurmycins |
| lusitanus | napthyridinomycin |
| peuceticus | daunomycin and adriamycin |
| violochromogenes | arugomycin |

TABLE V

β-Lactam Antibiotic-Producing Organisms

| Organism | Antibiotic |
|---|---|
| Cephalosporium various species | various β-lactams |
| Nocardia lactamadurans | cephamycin C |
| Penicillium various species | various β-lactams |
| Streptomyces | |
| antibioticus | clavulanic acid |
| argenteolus | asparenomycin A, MM 4550, and MM 13902 thienamycin |
| cattleya | thienamycin |
| chartreusis | SF 1623 and cephamycin A and B |
| cinnamonensis | cephamycin A and B |
| clavuligerus | PA-32413-I, cephamycin C, A16886A, clavulanic acid, and other clavams |
| fimbriatus | cephamycin A and B |
| flavovirens | MM 4550 and MM 13902 |
| flavus | MM 4550 and MM 13902 |
| fulvoviridis | MM 4550 and MM 13902 |
| griseus | cephamycin A and B |
| halstedi | cephamycin A and B |
| heteromorphus | C2081X and cephamycin A and B |
| hygroscopicus | deacetoxycephalosporin C |
| lipmanii | penicillin N, 7-methoxycephalosporin C, A16884, MM 4550, and MM 13902 (MM 17880) epithienamycin F, MM 4550, and MM 13902 |
| olivaceus | |
| panayensis | C2081X and cephamycin A and B |
| pluracidomyceticus | pluracidomycin A |
| rochei | cephamycin A and B |
| sioyaensis | MM 4550 and MM 13902 |
| sp. OA-6129 | OA-6129A |
| sp. KC-6643 | carpetimycin A |
| tokunomensis | asparenomycin A |
| viridochromogenes | cephamycin A and B |
| wadayamensis | WS-3442-D |

TABLE VI

Macrolide, Lincosamide, and Streptogramin Antibiotic-Producing Organisms

| Organism | Antibiotic |
|---|---|
| Micromonospora rosaria | rosaramicin |
| Streptomyces | |
| albireticuli | carbomycin |
| albogriseolus | mikonomycin |
| albus | albomycetin |
| albus var. coilmyceticus | coleimycin |
| ambofaciens | spiramycin and foromacidin D |
| antibioticus | oleandomycin |
| avermitilis | avermectins |
| bikiniensis | chalcomycin |
| bruneogriseus | albocycline |
| caelestis | M188 and celesticetin |
| cinerochromogenes | cineromycin B |
| cirratus | cirramycin |
| deltae | deltamycins |
| djakartensis | niddamycin |
| erythreus | erythromycins |
| eurocidicus | methymycin |
| eurythermus | angolamycin |
| fasciculus | amaromycin |
| felleus | argomycin and picromycin |
| fimbriatus | amaromycin |
| flavochromogenes | amaromycin and shincomycins |
| fradiae | tylosin |
| fungicidicus | NA-181 |
| fungicidicus var. espinomyceticus | espinomycins |
| furdicidicus | mydecamycin |
| goshikiensis | bandamycin |
| griseofaciens | PA133A and B |
| griseoflavus | acumycin |
| griseofuscus | bundlin |
| griseolus | griseomycin |
| griseospiralis | relomycin |
| griseus | borrelidin |
| griseus ssp. sulphurus | bafilomycins |
| halstedi | carbomycin and leucanicidin |
| hygroscopicus | tylosin |
| hygroscopicus subsp. aureolacrimosus | milbemycins |
| kitastoensis | leucomycin A3 and josamycin |
| lavendulae | aldgamycin |
| lincolnensis | lincomycin |
| loidensis | vernamycin A and B |
| macrosporeus | carbomycin |
| maizeus | ingramycin |
| mycarofaciens | acetyl-leukomycin, and espinomycin |
| narbonensis | josamycin and narbomycin |
| narbonensis var. josamyceticus | leucomycin A3 and josamycin |
| olivochromogenes | oleandomycin |
| platensis | platenomycin |
| rimosus | tylosin and neutramycin |
| rochei | lankacidin and borrelidin |
| rochei var. volubilis | T2636 |
| roseochromogenes | albocycline |
| roseocitreus | albocycline |
| spinichromogenes var. suragaoensis | kujimycins |
| tendae | carbomycin |
| thermotolerans | carbomycin |
| venezuelae | methymycins |
| violaceoniger | lankacidins and lankamycin |

TABLE VII

Miscellaneous Antibiotic-Producing Streptomyces

| Antibiotic Type | Streptomyces Species | Antibiotic |
|---|---|---|
| amino acid analogues | sp. | cycloserine |
| cyclopentane ring-containing | coelicolor | methylenomycin A |
| | erythrochromogenes | sarkomycin |
| | violaceoruber | methylenomycin A |
| nitro-containing | venezuelae | chloramphenicol |
| polyenes | griseus | candicidin |
| | nodosus | amphotericin B |
| | noursei | nystatin |

TABLE VII-continued

Miscellaneous Antibiotic-Producing Streptomyces

| Antibiotic Type | Streptomyces Species | Antibiotic |
|---|---|---|
| tetracyclines | aureofaciens | tetracycline, chlortetracycline, demethyltetracycline, and demethylchlortetracycline |
| | rimosus | oxytetracycline |

TABLE VIII

Nucleoside Antibiotic-Producing Organisms

| Organism | Antibiotic |
|---|---|
| Corynebacterium michiganese pv. rathayi | tunicamycin analogues |
| Nocardia candidus | pyrazofurin |
| Streptomyces | |
| antibioticus | ara-A |
| chartreusis | tunicamycin |
| griseoflavus var. thuringiensis | streptoviridans |
| griseolus | sinefungin |
| lysosuperificus | tunicamycin |

TABLE IX

Peptide Antibiotic-Producing Organisms

| Organism | Antibiotic |
|---|---|
| Actinoplanes | |
| missouriensis | actaplanin |
| teichomyceticus | teicoplanin |
| Bacillus various species | bacitracin, polymixin, and colistin |
| Nocardia | |
| candidus | A-35512 and avoparcin |
| lurida | ristocetin |
| orientalis | vancomycin |
| Streptomyces | |
| antibioticus | actinomycin |
| aureus | thiostrepton |
| canus | amphomycin |
| eburosporeus | LL-AM374 |
| haranomachiensis | vancomycin |
| pristinaespiralis | pristinamycin |
| roseosporus | lipopeptides, such as A21978C |
| toyocaensis | A47934 |
| virginiae | A41030 |

TABLE X

Polyether Antibiotic-Producing Organisms

| Organism | Antibiotic |
|---|---|
| Actinomadura various species | various polyethers |
| Dactylosporangium various species | various polyethers |
| Nocardia various species | various polyethers |
| Streptomyces | |
| albus | A204, A28695A and B, and salinomycin |
| aureofaciens | narasin |
| cacaoi var. asoensis | lysocellin |
| chartreusis | A23187 |
| cinnamonensis | monensin |
| conglobatus | ionomycin |
| eurocidicus var. asterocidicus | laidlomycin |
| flaveolus | CP38936 |
| gallinarius | RP 30504 |
| griseus | grisorixin |
| hygroscopicus | A218, emericid, DE3936, A120A, A28695A and B, etheromycin, and dianemycin |
| lasaliensis | lasalocid |
| longwoodensis | lysocellin |
| mutabilis | S-11743a |
| ribosidificus | Ionomycin |

TABLE X-continued

Polyether Antibiotic-Producing Organisms

| Organism | Antibiotic |
|---|---|
| violaceoniger | nigericin |
| Streptoverticillium various species | various polyethers |

The vectors of the present invention confer picromycin resistance to the picromycin-sensitive Streptomyces and related host cells described above. These vectors also confer resistance to the macrolide antibiotics rosaromycin, spiramycin, erythromycin and lincomycin. Although 20 µg/ml of picromycin is generally toxic to picromycin-sensitive Streptomyces, vectors of the present invention confer resistance to much higher levels of macrolide. For example, S. griseofuscus is normally sensitive to 25 µg/ml of tylosin, but upon transformation with a vector containing the picA gene, S. griseofuscus can tolerate levels of tylosin up to 50 µg/ml. Upon pre-treatment of the transformed cells with ~0.1-10 g/ml picromycin, the cells may become induced to withstand up to 500 µg/ml of tylosin. Furthermore, this induction will occur under low concentrations of erythromycin and rosaromycin. Various induction and resistance patterns are presented in Tables XI and XII. The preferred picromycin concentration for purposes of selection for Streptomyces species is readily determined by procedures well known in the art. While all embodiments of the present invention are useful, some of the vectors and transformants are preferred. Accordingly, Streptomyces griseofuscus is the preferred host for preferred plasmids pOJ321, pFJ370 and pFJ371.

The recombinant DNA vectors of the present invention have broad utility and help fill the need for suitable cloning vehicles for use in Streptomyces and related organisms. More particularly, the present vectors are used as a means for selecting a recombinant DNA-containing Streptomyces host cell. This is accomplished by transforming a picromycin-sensitive, preferably restrictionless Streptomyces host cell with one of the present vectors, such as pFJ370, and culturing the transformed cell under conditions suitable for selection for picromycin resistance or other macrolide resistance. Moreover, the ability of the present vectors to confer picromycin resistance provides a functional means for selecting transformants. This is important because of the practical necessity for determining and selecting the particular cells that have acquired vector DNA. Additional DNA segments, that lack functional tests for their presence, can also be inserted onto the present vectors and then transformants containing the non-selectable DNA can be isolated by picromycin selection. Such non-selectable DNA segments can be inserted at any site, except within regions necessary for plasmid function and replication or within the picromycin resistance-conferring gene, and include, but are not limited to, genes that specify antibiotic modification enzymes and regulatory genes of all types.

The functional test for picromy in resistance, described above, is also used to locate DNA segments that act as control elements and direct expression of an individual antibiotic resistance-conferring gene. Such segments, including, but not limited to, promoters, attenuators, repressors, inducers, ribosome-binding sites, and the like, are used to control the expression of other genes in Streptomyces and related organisms.

The picromycin resistance-conferring vectors of the present invention are also useful for ensuring that linked DNA segments are stably maintained in host cells over many generations. These genes or DNA fragments, covalently linked to the picromycin resistance-conferring DNA and propagated in Streptomyces, are maintained by exposing the transformants to levels of picromycin toxic to non-transformed cells. Therefore, transformants that lose the vector, and consequently lose any covalently linked DNA, cannot grow and are eliminated from the culture. Thus, the vectors of the present invention can stabilize and maintain DNA sequences of interest.

The cloning vectors and transformants of the present invention provide vehicles for the cloning of genes to improve yields of various products that are currently produced in Streptomyces and related cells. Examples of such products include, but are not limited to, streptomycin, tylosin, cephalosporins, actaplanin, narasin, monensin, tobramycin, erythromycin, and the like. The present invention also provides selectable vectors that are useful for cloning, characterizing, and reconstructing DNA sequences that code for: commercially important proteins such as, for example, human insulin, human proinsulin, glucagon, interferon and the like; enzymatic functions in metabolic pathways leading to commercially important processes and compounds; or control elements that improve gene expression. These desired DNA sequences also include, but are not limited to, DNA that codes for enzymes that catalyze synthesis of derivatized antibiotics such as, for example, streptomycin, cephalosporin, tylosin, actaplanin, narasin, monensin and erythromycin derivatives, or for enzymes that mediate and increase bioproduction of antibiotics or other products. The capability for isolating and using such DNA segments allows for increasing the yield and availability of antibiotics that are produced by Streptomyces and related organisms.

Streptomyces can be cultured in a number of ways using any of several different media. Preferred carbohydrate sources in a culture medium include, for example, molasses, glucose, dextrin, and glycerol. Nitrogen sources include, for example, soy flour, amino acid mixtures, and peptones. Nutrient inorganic salts are also incorporated and include the customary salts capable of yielding sodium, potassium, ammonium, calcium, phosphate, chloride, sulfate, and like ions. As is necessary for the growth and development of other microorganisms, essential trace elements are also added. Such trace elements are commonly supplied as impurities incidental to the addition of other constituents of the medium.

Streptomyces are grown under aerobic culture conditions over a relatively wide pH range of about 5 to 9 at temperatures ranging from about 15° to 40° C. For plasmid stability and maintenance, it is desirable to start with a culture medium at a pH of about 7.2 and maintain a culture temperature of about 30° C.

The following examples further illustrate and describe the invention disclosed herein. The invention is not limited in scope by reason of any of the following Examples; sources of reagents or equipment are provided merely for convenience and in no way limit the invention. Both an explanation of and the actual procedures for constructing the invention are described where appropriate.

EXAMPLE 1

Isolation of Plasmid pIJ702

A. Culture of *Streptomyces lividans* /pOJ702

Plasmid pIJ702 is disclosed in U.S. Pat. No. 4,666,846, the teaching of which is herein incorporated by reference. About $10^8$ spores of *Streptomyces lividans* /pIJ702 (NRRL 39155) are inoculated into 10 ml of TSB medium (Trypticase Soy Broth*) containing 25 μg/ml thiostrepton and grown with aeration at 29° C. until the culture is in early stationary phase. The culture is then homogenized, and 5 ml of the homogenized culture are used to inoculate 100 ml of TSB also containing thiostrepton. The 100 ml of culture are incubated at 29° C. with aeration until the Streptomyces lividans /pIJ702 cells reach stationary phase.

*TSB is made at 30 g/l and is obtained from
Baltimore Biological Laboratories (BBL),
P.O. Box 243, Cockeysville, Md. 21031.

B. Plasmid Isolation

The cells are collected and washed once with a 10.3% sucrose solution. The cells are then suspended in 24 ml of 10.3% sucrose, and 6 ml of 5X lysozyme solution (125 mM Tris-HCl, pH=8; 125 mM $Na_2$EDTA, pH=8; 10 mg/ml lysozyme; and 10.3% sucrose) are added. The solution is mixed and then incubated at 30° C. for 30–60 minutes, and then, about 18 ml of a solution that is 0.3 M NaOH, 1% SDS, and prewarmed to 50° C. are added, mixed and the resulting mixture is incubated at 80° C. for 10 minutes. The mixture is then cooled to room temperature, and 12 ml of a solution made by mixing 500 g phenol and 500 g $CHCl_3$ in 200 ml $H_2O$ are added and mixed well with the cell-extract. The phases are separated by centrifugation at 6000–8000 rpm for 10 minutes; approximately 45 ml of the resulting upper phase are transferred to a clean bottle.

Next, 4.5 ml of 3 M sodium acetate (NaOAc) and 50 ml of isopropanol are added to the supernatant, and the solution is mixed and left at room temperature for 30 minutes. The solution is then centrifuged (8000 rpm for 30 minutes) and the resulting supernatant discarded. The pellet is resuspended in 10 ml of TE buffer (10 mM Tris-HCl, pH=8, and 1 mM EDTA) containing 9.5 g of CsCl. About 1 ml of a 5 mg/ml solution of ethidium bromide is added to the solution to bring the final volume to 12.5 ml. The solution is then centrifuged at 52,000 rpm for 48 hours at 20° C. in a Beckman Ti-75 fixed-angle rotor. The fraction containing the plasmid band is extracted 5 times with isopropanol saturated with 20X SSC (0.3 M NaCl and 0.3 M NaCitrate) to remove the ethidium bromide. After the extractions, the sample is dialyzed against 1000 volumes of $H_2O$ and then against 1500 volumes of TE buffer. The procedure yields about 100 μg of plasmid pIJ702 DNA at a concentration of ~0.2 μg/ml and is stored at 4° C.

EXAMPLE 2

Construction of Plasmids pFJ370 and pJF371

A. Isolation of Plasmid pOJ160

Plasmid pOJ160 can be obtained from the Northern Regional Research Center in *E. coli* K12 JM109 under the accession number NRRL B-18088. The lyophils of *E. coli* K12 JM109/pOJ160 are plated onto L-agar plates (10 g of Bacto-tryptone, 10 g of NaCl, 5 g of Bacto-Yeast Extract, and 15 g of agar per liter) containing 200 μg/ml apramycin to obtain a single colony isolate of the strain. This colony is used to inoculate about 500 ml of L broth (L agar without agar) containing 200 μg/ml apramycin, and the resulting culture is incubated at 37° C. with aeration until the cells reach stationary phase.

Plasmid DNA is obtained from the cells to use in the construction of plasmids pFJ370 and pFJ371 in accordance with the following procedure, which is adapted from Maniatis et al., 1982, *Molecular Cloning* (Cold Spring Harbor Laboratory). This same procedure is used but on a smaller scale and with the ultracentrifugation steps replaced with phenol followed by chloroform extractions, to prepare the plasmid DNA used to identify the *E. coli* K12 294/pFJ370 and pFJ371 transformants.

About 500 ml of stationary-phase *E. coli*/pOJ160 cells are harvested by centrifugation at 4000Xg for 10 minutes at 4° C., and the supernatant is discarded. The cell pellet is washed in 100 ml of ice-cold STE buffer (0.1 M NaCl; 10 mM Tris-HCl, pH 7.8; and 1 mM EDTA). After the cell pellet is washed, the pellet is resuspended in 10 ml of Solution 1 (50 mM glucose; 25 mM Tris-HCl, pH=8 0; and 10 mM EDTA) that contains 5 mg/ml lysozyme and is left at room temperature for 10 minutes. Twenty ml of Solution 2 (0.2 N NaOH and 1% SDS are then added to the lysozyme-treated cells, and the solution is gently mixed by inversion. The mixture is incubated on ice for 10 minutes.

Fifteen ml of ice-cold, 3 M sodium acetate, pH=4.8, are added to the lysed-cell mixture, and the solution is mixed by inversion. The solution is incubated on ice for 60 minutes. The 3 M sodium acetate solution is prepared by mixing equal volumes of 3 M acetic acid and 3 M sodium acetate.

The lysed cell mixture is centrifuged in a Beckman SW27 rotor (or its equivalent) at 20,000 rpm for 20 minutes at 4° C. About 36 ml of supernatant are recovered, and 2.5 volumes of ethanol are added, mixed, and the resulting solution left on ice for 15 minutes. The plasmid DNA is collected by centrifugation at 12,000 Xg for 30 minutes at room temperature. The supernatant is discarded, and the DNA pellet is washed with 70% ethanol at room temperature. The ethanol wash is decanted, and the pellet is dried in a vacuum desiccator. The pellet is then resuspended in 8 ml of TE buffer.

Eight grams of CsCl are added to the DNA solution. About 0.8 ml of a 10 mg/ml solution of ethidium bromide in water are added for each 10 ml of CsCl-DNA solution. The final density of the solution is about 1.55 g/ml, and the ethidium bromide concentration is about 800 μg/ml. The solution is transferred to a Beckman Type 50 centrifuge tube, filled to the top with TE buffer containing 1.55 g/ml CsCl, sealed, and centrifuged at 45,000 rpm for 24 hours at 20° C. After centrifugation, two bands of DNA are visible in ordinary light and become even more prominent in UV light. The cap is removed from the tube, and the lower DNA band is recovered using a syringe with a #21 hypodermic needle inserted through the side of the centrifuge tube.

The ethidium bromide is removed from the solution of plasmid DNA by several extractions with water-saturated 1-butanol, and the CsCl is removed by dialysis against TE buffer. After extractions with buffered phenol and then chloroform, the DNA is precipitated, washed with 70% ethanol, and dried. About 0.5 mg of plasmid pOJ160 DNA can be obtained by this procedure.

B. Final Construction of Plasmids pOJ370 and pOJ371

Plasmid pOJ321 is isolated from *E. coli* K12 JM109/pOJ321 in substantial accordance with the teaching of Example 2A. A culture of *E. coli* K12 JM109/pOJ321 is on deposit at the National Regional Research Laboratory in Peoria, Ill. under the accession number NRRL B-18389. A restriction site and function map of plasmid pOJ321 is presented in FIG. 1 of the accompanying drawings.

About 10 μg (10 1) of plasmid pOJ321 DNA is added to 2 μl of 10X PvuII buffer (100 mM Tris-HCl, pH=8.0; 0.5 M NaCl; and 100 mM $MgCl_2$), 7 μl of H20, and 1 μl (~15 units; unit definitions herein correspond to those of New England Biolabs, 32 Tozer Road, Beverly, Mass. 01915-9990, unless otherwise indicated) of restriction enzyme PvuII. The resulting reaction is incubated at 37° C. for two hours. The reaction mixture is extracted with 100 μl of a 1:1 solution of phenol:-chloroform and then with 100 μl of chloroform. The PvuII-digested DNA is collected by adjusting the sodium acetate (NaOAc) concentration of the reaction mixture to 0.30 M, adding 2.5 volumes of ethanol, chilling the reaction mixture to −70° C., and centrifuging to pellet the precipitated DNA. The PvuII-digested plasmid pOJ321 DNA is resuspended in 1 μl of water.

About 10 μg of plasmid pOJ160 in 100 μl of TE buffer are added to 13 1 of 10X PvuII buffer, 13 μl of $H_2O$ and 4 μl (~60 units) of restriction enzyme PvuII. The resulting reaction is incubated at 37° C. for 5 minutes. This results in a partial digestion of the plasmid with restriction enzyme PvuII. The reaction mixture contains uncut plasmid pOJ160, totally digested plasmid pOJ160, and plasmid pOJ160 which has been cleaved at only one, two or three of the four PvuII sites. The reaction mixture is extracted and the DNA is precipitated as described above. The DNA is then redissolved in 100 μl of water, to which 20 μl of 10X BAP buffer (0.5 M Tris HCl, pH 8.0, 0.5 M NaCl) and 80 μl of bacterial alkaline phosphatase (BAP, 24 μ/ml) are added. Dephosphorylation is allowed to occur for one hour at 70° C. The DNA is extracted and precipitated as before and resuspended in 10 μl of water.

The PvuII-digested plasmid pOJ321 DNA is then electrophoresed on a 1% agarose gel until the desired ~2.8 kb PvuII restriction fragment is clearly separated from the other digestion products. Visualization of the electrophoresed DNA is accomplished by staining the gel in a dilute solution (0.5 μg/ml) of ethidium bromide and exposing the stained gel to long-wave UV light. After the desired fragment is located, a small slit is made in the gel in front of the fragment, and a small piece of Schleicher and Schuell (Keene, N.H. 03431) NA-45 DEAE membrane was placed in the slit. Upon further electrophoresis, the ~2.8 kb PvuII restriction fragment is non-covalently bound to the DEAE membrane. After the desired fragment is bound to the DEAE membrane, the membrane is removed and rinsed with low salt buffer (150 mM NaCl; 0.1 mM EDTA; and 20 mM Tris-HCl, pH=8). Next, the membrane is placed in a small tube and immersed in high salt buffer (1 M NaCl; 0.1 mM EDTA; and 20 mM Tris-HCl, pH=8) and then incubated at 65° C. for one hour to elute the DNA from the DEAE paper. After the 65° C. incubation, the incubation buffer is collected and the membrane rinsed with high salt buffer. The rinse solution is pooled with the incubation buffer before collecting the desired DNA fragments.

About three volumes of cold, absolute ethanol are added to the high salt-DNA solution. The resulting solution is mixed and placed on ice for 10-20 minutes and then centrifuged at 15,000 rpm for 15 minutes. After another precipitation to remove residual salt, the DNA pellet is rinsed with ethanol, dried, resuspended in 50 μl of TE buffer.

In the same manner, the partially digested PvuII fragments of plasmid pOJ160 are electrophoresed and the linear DNA is isolated and purified. This linear DNA corresponds to plasmid pOJ160 which has only been cleaved at one of the four possible PvuII sites. The purified, linear, partially-digested plasmid pOJ160 is then resuspended in 50 μl of TE buffer.

The partially PvuII-digested plasmid pOJ160 DNA (1 μl) is added to 10 μl (~0.5 μg) of the ~2.8 kb, picA-containing PvuII restriction fragment of plasmid pOJ321, 2 μl of 10X ligase buffer (660 mM Tris-HCl, pH=8; 66 mM MgCl ; 10 mM dithiothreitol (DTT); and 10 mM ATP), and 6 μl of $H_2O$. About 1 μl (~100 units) of T4 DNA ligase is added to the solution of DNA, and the resulting reaction is incubated at 15° C. overnight (~16 hours). The ligation yields various constructions and formations which contain the ~2.8 kb PvuII fragment of plasmid pOJ321. Two specific constructions constitute plasmids pFJ370 and pFJ371. Restriction site and function maps of plasmids pFJ370 and pFJ371 are presented in FIG. 2 of the accompanying drawings.

To prepare *E. coli* K12 294 cells that are competent for transformation, the lyophils of *E. coli* K12 294 obtained from the ATCC (accession number ATCC 31446) are reconstituted to isolate single colonies. One single-colony isolate of 294 is inoculated into 5 ml of L broth (10 g of Bacto-tryptone, 10 g of NaCl, and 5 g of Bacto-Yeast Extract per liter) that contains 10 mM $MgSO_4$ and 10 mM $MgCl_2$, and the culture is incubated at 37° C. overnight with aeration. Fifty μl of the overnight culture are used to inoculate 5 ml of L broth that contains 10 mM $MgSO_4$ and 10 mM $MgCl_2$. The culture is incubated at 37° C. overnight with aeration. The following morning, the culture is diluted to 200 ml with L broth that contains 10 mM $MgSO_4$ and 10 mM $MgCl_2$. The diluted culture is incubated at 37° C. with aeration until the absorbance at 550 nm (Asso) is about 0.5, which indicates a cell density of about $1 \times 10^8$ cells/ml. The culture is cooled for ten minutes in an ice-water bath, and the cells are then collected by centrifugation at 4000 Xg for 10 minutes at 4° C. The cell pellet is resuspended in 100 ml of cold 10 mM NaCl and then immediately repelleted by centrifugation. The cell pellet is resuspended in 100 ml of 30 mM $CaCl_2$ and incubated on ice for 20 minutes.

The cells are again collected by centrifugation and resuspended in 10 ml of 30 mM $CaCl_2$. A one-half ml aliquot of the cells was added to the ligated DNA prepared above. The cell-DNA mixture is incubated on ice for one hour, heat-shocked at 42° C. for 90 seconds, and then chilled on ice for about two minutes. The cell-DNA mixture is centrifuged, and the cell pellet is resuspended into 0.5 ml of L broth in a 1.5 ml tube and incubated at 37° C. for one hour.

Aliquots of the transformation mixture are plated on L-agar (L-broth with 15 grams per liter agar) plates containing 200 μg apramycin/ml. The plates are incubated at 37° C. overnight. Several apramycin-resistant colonies are selected and then screened by restriction enzyme analysis of their plasmid DNA for the presence of the ~2.8 kb PvuII restriction fragment. Plasmid DNA is obtained from the *E. coli* K12 194 pFJ370 and pFJ371 transformants in accordance with the procedure for isolating plasmid pOJ160 DNA, described above. The plasmids pFJ370 and pFJ371 DNA can be used to transform *Streptomyces griseofucus* C581 to picromycin resistance, ad described in Example 3, below.

EXAMPLE 3

Construction of Picromycin-Resistant *Streptomyces griseofuscus* C581

A. List of Solutions

The following solutions are referred to throughout the Examples and are presented here for clarity.

| Ingredient | Amount |
|---|---|
| 1. P medium (~100 ml): | |
| Sucrose | 10.3 g |
| $K_2SO_4$ | 0.025 g |
| Trace element solution (see #3) | 0.2 ml |
| $MgCl_2.6H_2O$ | 0.203 g |
| Water | 80 ml |
| After autoclaving add: | |
| $KH_2PO_4$ (0.5%) | 1 ml |
| $CaCl_2.2H_2O$ (3.68%) | 10 ml |
| (N-tris-(hydroxymethyl)-methyl-2-aminoethane sulphonic acid), "TES" buffer, 0.25 M, pH = 7.2 | 10 ml |
| 2. Trace element solution (~1 L): | |
| $ZnCl_2$ | 40 mg |
| $FeCl_3.6H_2O$ | 200 mg |
| $CuCl_2.2H_2O$ | 10 mg |
| $MnCl_2.4H_2O$ | 10 mg |
| $Na_2B_4O_7.10H_2O$ | 10 mg |
| $(NH_4)_6Mo_7O_{24}.4H_2O$ | 10 mg |
| $H_2O$ | 1 L |
| 3. R2 Regeneration Medium (~1 L): | |
| Sucrose | 103 g |
| $K_2SO_4$ | 0.25 g |
| Trace element solution | 2 ml |
| $MgCl_2.6H_2O$ | 10.12 g |
| glucose | 10 g |
| L-asparagine.$1H_2O$ | 2.0 g |
| casamino acids | 0.1 g |
| Agar | 22 g |
| Water | to 700 ml |
| The pH is adjusted to pH = 7.2 before autoclaving. After autoclaving, add: | |
| $KH_2PO_4$ (0.05 g/100 ml) | 100 ml |
| $CaCl_2$ (2.22 g/100 ml) | 100 ml |
| TES Buffer (5.73 g/100 ml, pH = 7.2) | 100 ml |
| 4. Soft nutrient agar (SNA, ~1 L): | |
| Difco Bacto Nutrient Broth | 8 g |
| Agar | 5 g |
| 5. R2YE medium is R2 medium with 20 ml of 25% yeast extract added per liter. | |
| 6. Yeast Extract - Malt Extract (YEME, ~1 L): | |
| Yeast extract | 3 g |
| Peptone | 5 g |
| Malt extract | 3 g |
| Glucose | 10 g |
| 7. YEME + 34% Sucrose Liquid Complete Medium is YEME with 340 g/L of sucrose. | |
| 8. YMX Media (~1 L): | |
| Yeast extract | 3 g |
| Malt extract | 3 g |
| Glucose | 2 g |
| Agar | 20 g |
| 9. YMX Agar is 0.3% yeast extract, 0.3% malt extract, 0.2% dextrose, and 2.0% agar. | |

B. Transformation of *Streptomyces griseofucus*

*Streptomyces griseofuscus* C581 (ATCC 23916) is plated on YMX agar and incubated at 30° C. for about 72 hours. A plug of cells is removed from the plate and used to inoculate 10 ml of TSB. The culture is homogenized and incubated at 30° C. for ~30 hours. About 4 ml of this culture are homogenized and used to inoculate 100 ml of TSB containing 0.4% glycine. The culture is incubated at 30° C. for about 24 hours. About 4 ml of this culture are again homogenized and used to inoculate 100 ml of TSB containing 0.4% glycine. The culture is incubated at 30° C. for about 16 hours. The cells are harvested and washed three times with 10.3% sucrose. The cells are resuspended in 100 ml of P media containing 1 mg/ml lysozyme, and the resulting solution is incubated at 30° C. for 2 hours. During this protoplasting step, the cells are pipetted up and down to disperse clumps. The protoplasts are collected and washed three times with P medium. The protoplasts are then suspended in 10 ml of P medium. This process usually generates about 2 to $5 \times 10^7$ protoplasts per 150 $\mu$l of solution.

Approximately 150 $\mu$l of the protoplast solution are added to 10 $\mu$l of the transforming DNA, either in ligation or TE buffer, and mixed. About 100 $\mu$l of 50% polyethylene glycol 1000 in P media are then added and mixed. After a brief (1 to 2 minutes) incubation at room temperature, the cell-DNA mixture is brought to a volume of 1 ml by the addition of P media. The cell suspension is plated onto R2 medium; about 0.1 ml of cells is inoculated per R2 plate. The plates are incubated at 30° C. overnight (~16 hours) and then overlaid with ~3 ml of R2-modified agar (103 g sucrose, 10.12 g MgCl$_2$, 2.22 g CaCl$_2$, and 5.72 g TES at pH=7.2 per liter) containing enough thiostrepton to give a final concentration, after diffusion, of 25 $\mu$g/ml. The plates are then incubated for about four days at 30° C., when colonies become visible to the naked eye.

Spiramycin-resistant transformants are selected by patching regenerated protoplasts to R2 medium containing 25 $\mu$g/ml of spiramycin. The plates may also contain 25 $\mu$g/ml of either erythromycin (available from sigma Chemical Co, P.O. Box 14508, St. Louis, Mo. 63178) or rosaromycin (available from Schering Corp., Galloping Hill Road, Kenilworth, N.J. 07033). Alternatively, picromycin-resistant transformants are selected by inoculating the regenerated protoplasts into TSB containing 0.5 $\mu$g/ml picromycin. Picromycin may be produced and purified in substantial accordance with the teaching of U.S. Pat. No. 2,693,433, the teaching of which is herein incorporated by reference. The culture is incubated for 16–22 hours at 30° C. before plating the cells onto media containing 10 $\mu$g/ml picromycin. As plasmids pFJ370 and pFJ371 also comprise a thiostrepton resistance-conferring gene, thiostrepton, at a final concentration of 20 $\mu$g/ml, is also used to select transformants.

The transformants are cultured on R2 agar supplemented with picromycin (10 $\mu$g/ml) to obtain single colonies. These single colonies are used to inoculate 10 ml TSB cultures containing both picromycin and thiostrepton (25 $\mu$g/ml). The cultures were homogenized and then grown overnight at 30° C. in a rotary shaker.

Plasmid isolation for analysis is done by a small-scale version of the protocol of Example 1; the CsCl gradients of Example 1 were replaced by ethanol precipitations. The mycelium is collected by centrifugation, washed twice with 10.3% sucrose and then suspended in 1–2 ml of 10.3% sucrose. Four hundred $\mu$l of the cell mixture are transferred to a small tube, and 100 $\mu$l of 5X Lysozyme solution (Example 1) are added. The suspension is incubated at 30° C. for 30–60 minutes, followed by the addition and mixing of 300 $\mu$l of 0.3 M NaOH containing 1% SDS. The latter solution is kept at 50° C. before its addition to the cell mix. The cell mixture is placed at 80° C. for 10 minutes, cooled to room temperature, and then extracted with 200 $\mu$l of phenol:CHCl$_3$ (50:50). The aqueous phase is transferred to a clean tube, made 0.3 M in NaOAc, and then, one volume of isopropanol is added. The DNA is incubated at room temperature for five minutes and then pelleted by centrifugation. The pellet is dissolved in 500 $\mu$l of TE buffer, and about 25 $\mu$l of 0.1 M spermine are added to the solution of DNA, and the mixture is incubated at room temperature for 5 minutes. After centrifugation, the DNA pellet is rinsed with 75% ethanol, then resuspended and reprecipitated from 0.3 M sodium acetate using ethanol. After this last precipitation, the plasmid DNA is suspended in 50 $\mu$l of TE buffer. Restriction enzyme cutting and electrophoretic analysis of the reaction products are used to determine plasmid structure.

EXAMPLE 4

Construction of plasmids pFJ372 and pFJ373

About 1 $\mu$g of plasmid pIJ702, (isolated in Example 1), 25 $\mu$l of water, 5 $\mu$l BSA (1 mg/ml), 5 $\mu$l 10X BglII restriction buffer (200 mM Tris-HCl pH 8.0, 1 M NaCl, 70 mM MgCl$_2$ and 20 mM 2-mercaptoethanol) and 2 $\mu$l (~20 units) BglII restriction enzyme are mixed and incubated at 37° C. for 1 hour. This vector DNA is then precipitated, washed and dried. The 5' overhang is filled in using the DNA Polymerase I procedure essentially as described in Maniatis et al., 1982. This BglII cut, filled-in plasmid is then dephosphorylated in substantial accordance with the teaching of Example 2B. The ~2.8 kb PvuII-cut restriction fragment of plasmid pOJ321 is then ligated into the BglII-cut, filled-in, dephosphorylated plasmid pIJ702 in substantial accordance with the teaching of Example 2B. The ligation mixture is then transformed into Streptomyces griseofuscus in substantial accordance with the teaching of Example 3. The resultant plasmids pFJ372 and pFJ373, which differ only in the orientation of the picromycin resistance-conferring gene fragment, confer picromycin resistance to Streptomyces griseofuscus. Restriction and function maps of plasmids pFJ372 and pFJ373 are presented in FIG. 3 of the accompanying drawings.

EXAMPLE 5

Construction of Integrating plasmids pFJ374 and pFJ375

A. Preparation of Streptomyces felleus DNA

About 2.5 ml of fresh overnight culture of Streptomyces griseofuscus (ATCC 23916) is used to inoculate 50 ml of TSB (Trypticase Soy Broth). The culture is grown overnight at 30°–32° C. with vigorous shaking. The cells are harvested by centrifugation, suspended in 10 ml lysis buffer (15% Sucrose, 25 mM Tris-HCl pH 8.0, 50 mM EDTA) plus lysozyme (5 mg/ml) and incubated at 37° for 15 minutes. Then, 0.1 ml of 10 mg/ml Proteinase K (prepared fresh in lysis buffer) is added, along with 1.0 ml of 10% sodium dodecyl sulfate (SDS). This mixture is immediately incubated at 70° C. for 15 minutes and then cooled on ice. Next, 2.5 ml of 5 M potassium acetate is added and mixed by gentle inversion before placing on ice for 15 minutes. After gently extracting the material with TE saturated phenol, the layers are separated by centrifugation (10,000 rpm for 10 minutes) and the aqueous phase is transferred to a fresh tube using a pipet with the tip broken off. After gently extracting the material with an equal volume of Sevag, the layers are again separated, the aqueous phase transferred to a fresh tube and the DNA precipitated with ethanol (two volumes) at room temperature. The precipitate is washed with 70% ethanol and then dissolved in 5 ml of TE. RNase A (final concentration of 50 μg/ml) and RNase Tl (final concentration of 1 μg/ml) are added and this solution is incubated at 37° C. for 30 minutes. After extracting twice with phenol, twice with Sevag and then precipitating with ethanol (two volumes), the DNA is dried in vacuo and redissolved in TE (in 1 ml for a 50 ml culture). The DNA is sized on a 0.3% agarose gel.

Next, 200 μg of *Streptomyces griseofuscus* chromosomal DNA are incubated with 85 units (10 μl) of MboI in 100 μl BSA, 100 μl MboI restriction buffer (500 mM Tris-HCl pH 8.0, 100 mM MgCl$_2$, 50 mM NaCl) and ~800 μl water at 37° C. for three minutes. This particular condition was found, empirically, to give the desired suitable distribution of partially digested DNA. The DNA is extracted with phenol, Sevag, and precipitated with ethanol (1/10 volume of 3 M NaOAc, three volumes ethanol at −70° C. for 30 minutes). The precipitate is collected by centrifugation (15 minutes) in an Eppendorf centrifuge and then the DNA is dissolved in 125 μl of water. After saving ~5 μg of DNA for use in determining whether the subsequently performed dephosphorylation is complete, the rest of the DNA is added to 20 μl of 10 X bacterial alkaline phosphase (BAP) buffer and 80 μl (24 units/ml) of BAP. This mixture is incubated at 780° C. for one hour and then 80 μl of BAP is added and incubated for an additional hour. The DNA is extracted with phenol, Sevag, precipitated as taught directly above, and dissolved in 50 μl TE. The size of this DNA is estimated on a 0.3% agarose gel.

B. Final Construction of plasmids pFJ374 and pFJ375

The 5' overhangs of the chromosomal DNA isolated in Example 5A are filled in using the DNA Polymerase I procedure essentially as described in Maniatis et al., 1982. About 2 μg of pBR322 (BRL) are then digested to completion using EcoRI restriction enzyme in substantial accordance with the teaching of Example 2 except 10 X EcoRI buffer (1 M Tris-HCl, pH=7.5, 500 mM NacL and 500 mM Mgcl) is used. The 5' overhang of this EcoRI-cut pBR322 is filled in using the above mentioned DNA Polymerase I procedure. The MboI-cut, filledin chromosomal DNA and the EcoRI-cut, filled-in pBR322 are then ligated together in substantial accordance with the teaching of Example 2B. The ligation mix is transformed into competent *E. coli* 294 cells in substantial accordance with the teaching of Example 2B, selecting for tetracycline resistance. This intermediate plasmid, pFJ378, is then extracted from the transformed cells in substantial accordance with the procedure of Example 2.

Figure 4:
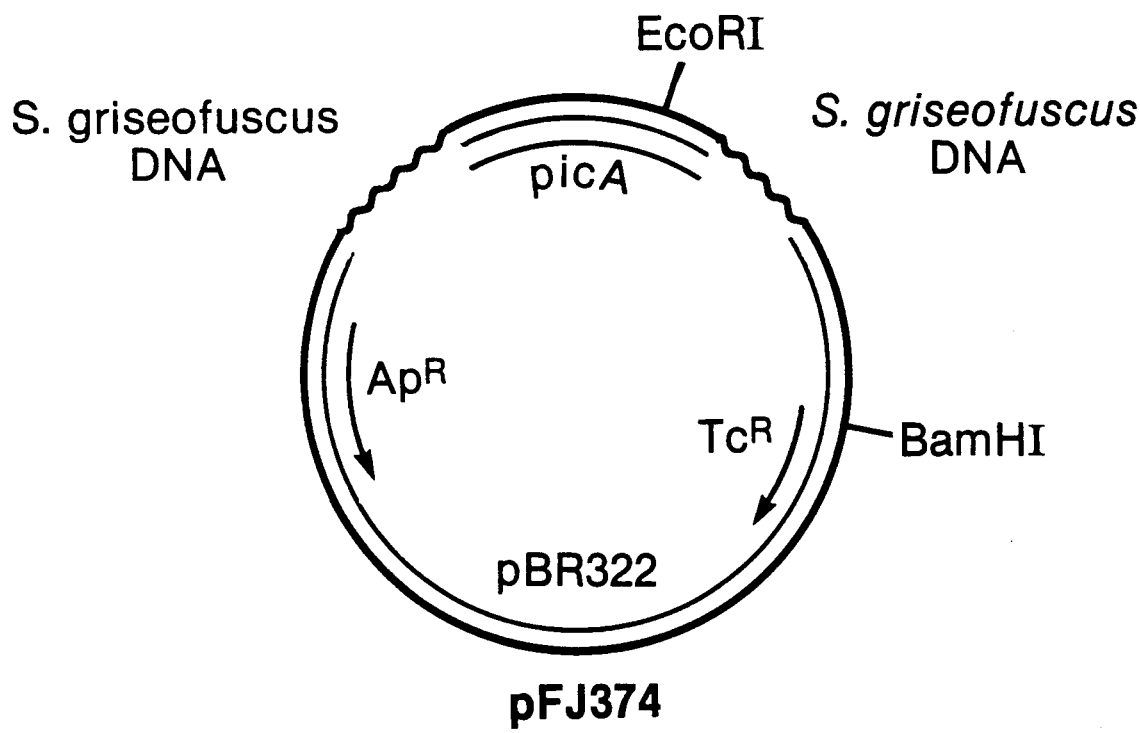
FIG. 4—the restriction site and function maps of plasmids pFJ374 and pFJ375.
Figure 4:
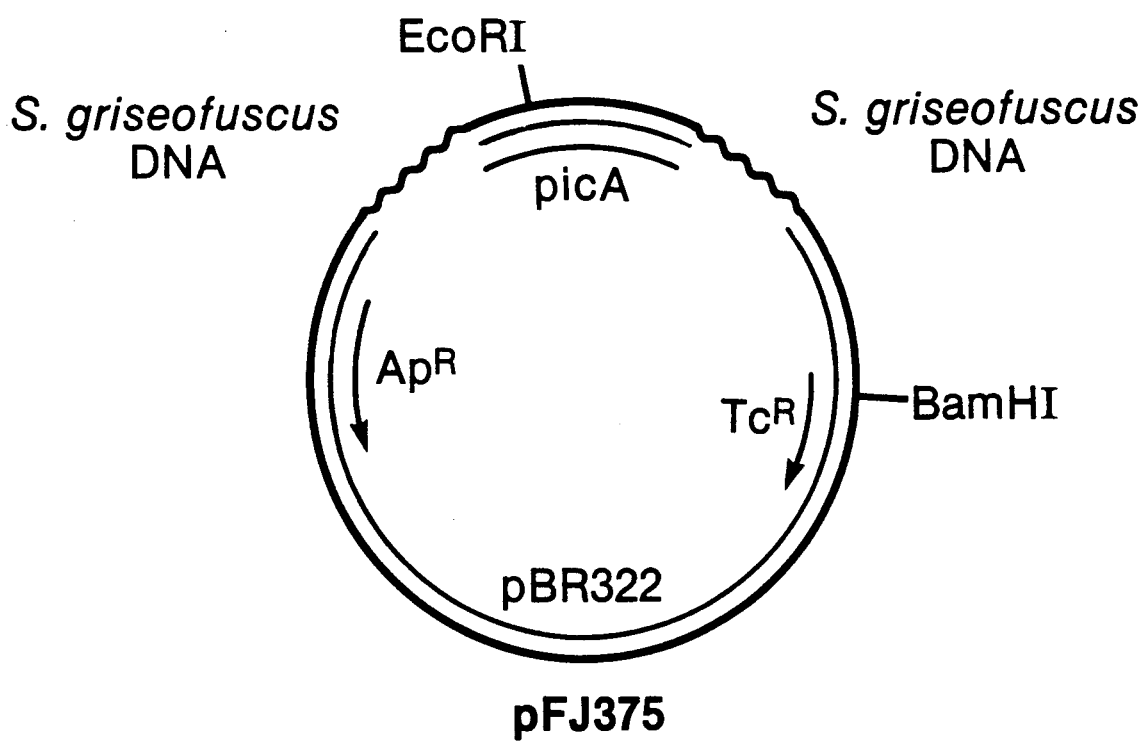

About 10 μl (~5 μg) of plasmid pFJ378, 25 μl water, 5 μl BSA, 5 μl 10 X PvuII restriction buffer (100 mM Tris-HCl pH 8.0, 0.5 M NaCl, 100 mM MgCl$_2$ and 20 mM 2-mercaptoethanol) and 1 μl PvuII enzyme are mixed and incubated at 37° C. for 4–5 minutes. A 10 μl aliquot is removed, mixed with 40 μl water and heated at 70° C. for 10 minutes to inactivate the enzyme. This protocol produces all possible reaction products ranging from molecules that have not been cleaved by the PvuII restriction enzyme to those that have been completely digested by the PvuII restriction enzyme. The aliquot is precipitated with 1/10 volume NaOAc pH 8.0 and 2 volumes ethanol and then frozen at −70° C. for 1 hour. This partially PvuII digested plasmid is then ligated to the ~2.8 kb PvuII restriction fragment of plasmid pOJ321 (isolated in example 2) in substantial accordance with the teaching of Example 2B. This ligation mixture is then transformed into *E. coli* 294 cells and the transformants are selected for ampicillin and tetracycline resistance. All transformants are pooled and the plasmid DNA is extracted in substantial accordance with the teaching of Example 2. The resultant plasmids, designated pFJ374 and pFJ375 differ only in respect to the orientation of the picA fragment, and are illustrated in FIG. 4 of the accompanying drawings.

About 2 μl of plasmid pFJ374 is used to transform *Streptomyces griseofuscus* protoplasts in substantial accordance with the teaching of Example 3B, except the protoplasts are overlain with R2 top agar containing enough picromycin to give a final concentration of 25 μg/ml. Plasmid pBR322 does not contain a Streptomyces replicon, so the only resistant colonies which arise are those in which the cells have undergone a crossover, homologous recombination and subsequent integration of the picA a gene into the Streptomyces genome.

EXAMPLE 6

Construction of Integrating phages pFJ376 and pFJ377

A. Culture of *E. coli* K12 BE447/pKC331

A 2 ml culture of *E. coli* K12 BE447/pKC331 (NRRL B-15828) is grown in the presence of 50 μg/ml ampicillin in TY media (1% tryptone, 0.5% NaCl and 0.5% yeast extract, pH 7.4) until the cells reach stationary phase. The 2 ml culture is then used to inoculate a flask containing 1 liter of TYH media containing 50 μg/ml ampicillin and growth continues until the optical density of the culture at 550 nanometers is between 0.50 and 0.75 absorbance units. When the O.D. 550 reaches and 0.50–0.75 range, 1 g of uridine is added, and, 15 minutes later, 170 mg of chloramphenicol is added. The incubation and culturing is then continued for 16 hours.

B. Isolation of Phasmid pKC331

The culture is centrifuged and the cell pellet resuspended in 10 ml of a solution that is 25% w/v sucrose; 50 mM Tris-HCl, pH=8; and 1 mM EDTA. Next 2 ml of 0.5 M EDTA and 2 ml of a 5 mg/ml lysozyme solution in 0.25 M Tris-HCl, pH=8 are added, and the resultant mixture is incubated at room temperature for 15 minutes. After incubation, about 14 ml of a solution that is 50 mM Tris-HCl, pH=8; 6 mM EDTA; and 0.1% Triton X-100 are added. The lysozyme-treated cells are then mixed by inversion.

The lysed cell mix is centrifuged until the cell debris forms a loose pellet. After the cell debris pellet is discarded and the supernatant extracted with buffered (pH=8) phenol, the aqueous phase is made 0.25 M in NaCl and two volumes of ethanol are added. The resultant mixture is chilled to −70° C., and the nucleic acid is pelleted by centrifugation. Further centrifugation (45,000 rpm for 16 hours at 20° C.) using cesium chloride gradients with ethidium bromide is carried out to purify the phasmid DNA. The desired phasmid pKC331 DNA is the collected and the ethidium bromide and cesium chloride removed by conventional procedures. The approximately 1 mg of phasmid pKC331 DNA obtained by this procedure is dissolved in 1 ml of TE buffer (10 mM Tris-HCl, pH 8 and 1 mM EDTA) and stored at −20° C.

C. PstI Digestion of Phasmid pKC331 and Isolation of the ~37 kb PstI Restriction Fragment About 10 μg (10 μl) of the phasmid pKC331 isolated in example 6B are added to 10 μl 10 X PstI salts, 2 μl restriction enzyme PstI (~10 Units) and 78 μl H₂O. After gentle mixing, the digest is allowed to react 2 hours at 37° C. and after digestion, the ~37 kb PstI fragment containing the phage θC31 sequences is purified by conventional electrophoretic gel means. The purified fragment obtained (~5 μg) is suspended in 5 μl of TE buffer.

D. T4 DNA Polymerase Treatment and Ligation of the ~2.8 kb Picromycin Resistance-Conferring PvuII Restriction Fragment to the ~37 Kb Pst I Restriction Fragment of Phasmid pKC331

The 3' overhangs on both ends of the TM 37 kb PstI restriction fragment of phasmid pKC331 are chewed back using the T4 DNA Polymerase procedure essentially as described in Maniatis et al., 1982. The ~37 kb PstI restriction fragment of phasmid pKC331 is then dephosphorylated in substantial accordance with the teaching of Example 2B. The ~2.8 kb PvuII restriction fragment from plasmid pOJ321 is then ligated into the ~37 kb fragment of pKC331 in substantial accordance with the teaching of Example 2B. This ligation produces desired phages pFJ376 and pFJ377, which differ only in respect to the orientation of the ~2.8 kb picA fragment. Restriction site and function maps of phages pFJ376 and pFJ377 are presented in FIG. 5 of the accompanying drawings. The ligated DNA is used to transform Streptomyces to obtain infective phage particles and the phage are then used to prepare picromycin-resistant Streptomyces via chromosomal integration of the vector.

EXAMPLE 7

Construction of Streptomyces griseofuscus/pFJ376 and Streptomyces griseofuscus/pFJ377

A vegetative inoculum is conventionally prepared by growing Streptomyces griseofuscus C581 (ATCC 23916) under submerged conditions for 20 hours at 30° C. in TSB supplemented with 0.4% glycine. The procedure for protoplasting S. griseofuscus is generally performed as follows. A culture of S. griseofuscus is spread on a plate containing YMX agar and incubated at 30° C. for approximately 48 hours. A single bacterial colony from the plate is then inoculated into 10 ml TSB; the culture is homogenized and then incubated at 30° C. overnight. About 4 ml of the overnight culture are homogenized, added to 100 ml TSB supplemented with 0.4% glycine and then incubated overnight at 30° C. This procedure is repeated, using the fresh overnight culture. About 50 ml of 50% (v/v) glycerol are then added to the culture and 15 ml samples are frozen and stored for up to six months at −20° C. The frozen cells are thawed by placing the tube at room temperature in a beaker of water. The cells are then harvested in a bench top centrifuge and washed three times in 10 ml of 10.3% sucrose. The cell pellet is resuspended in 10 ml of P medium supplemented with lysozyme (1 mg/ml) and incubated at 30° C. for 2 hours. The mixture is then centrifuged to pellet the protoplasts. The pellet is washed three times, using 10 ml P medium and vortexing the pellet into solution each wash. The protoplasts are resuspended in 2 ml P medium for subsequent transformation.

The ligated DNA of Example 6, 200 μl of Streptomyces griseofuscus protoplasts, $10^8$ spores of Streptomyces griseofuscus and 500 μl of 55% polyethylene glycol in P medium are vortexed and aliquots of 25 μl and 250 μl are plated onto R2YE plates with 3 ml of R2YE top agar. The plates are incubated at 37° C. Plaques can usually be seen after ~20 hours. After plaques appear, they are removed from the plate and the phage particles washed off the agar into TSB medium. Serial dilutions of the phage suspension are made and aliquots removed and mixed with $10^8$ spores of Streptomyces griseofuscus. These dilutions are made in order to achieve a good plaque distribution on the plate. The mixtures are plated on YMX plates and incubated at 30° C. until sporulation occurs, a process taking about 4 days. After sporulation, the plates are replica plated onto fresh YMX plates containing 25 μg/ml spiromycin or picromycin. The replica plates are then incubated at 30° C. for 3-4 days, and the resultant S. griseofuscus/pFJ376 or S. griseofuscus/pFJ377 picromycin-resistant colonies are isolated, cultured and identified according to known procedures.

EXAMPLE 8

Induction of multiple drug resistance using the picA gene

Upon transformation and/or integration of the picA gene into antibiotic sensitive strains of Streptomyces or Nocardia, the picA gene can be induced so as to confer higher levels of resistance to carbomycin, tylosin and spiramycin. This induction occurs when the cells containing picA are grown in media supplemented with ~0.1-10 μg/ml picromycin, rosaromycin or erythromycin. Table XI demonstrates the inductive pattern of the picA gene.

TABLE XI

| | Inducers of MLS Resistance in S. griseofuscus/picA | | | | | | | | | | | | |
|---|---|---|---|---|---|---|---|---|---|---|---|---|---|
| Inducer | Ery | | Tyl | | Ros | | Car | | Linc | | Spi | | Pc | |
| Resistance | $Car^{10}$ | $Tyl^{10}$ | $Car^{10}$ | $Tyl^{10}$ | $Car^{10}$ | $Tyl^{10}$ | $Car^{10}$ | $Tyl^{10}$ | $Car^{10}$ | $Tyl^{10}$ | $Car^{10}$ | $Tyl^{10}$ | $Car^{10}$ | $Tyl^{10}$ |
| Strain | | | | | | | | | | | | | | |
| No picA | − | − | − | − | − | − | − | − | − | − | − | − | − | − |
| picA | ++ | + | − | − | ++ | + | − | − | − | − | − | − | ++++ | +++ |

++++/strong growth +++/good growth ++/moderate growth +/weak growth −/no growth

The induced picA gene also confers higher levels of resistance to antibiotics than it would if it were uninduced. Table XII demonstrates this increase in resistance conferred by the picA gene.

TABLE XII

Increase in Resistance Conferred by the Induced picA Gene

| Strain | Uninduced S. felleus | | | | | | Uninduced S. griseofuscus |
|---|---|---|---|---|---|---|---|
| μg Conc, μg/ml Antibiotic | 10 | 50 | 100 | 250 | 500 | 1000 | Disc Assay Zone Size |
| PC | ND | ND | ND | ND | ND | ND | 25 mm |
| Ros | ++++ | ++++ | ND | ND | ND | ND | 37 mm |
| Linc | ++++ | ++++ | ++++ | ++++ | ++++ | ++++ | 12 mm |
| Spi | ++++ | ++++ | ++++ | ++++ | ++++ | ++++ | 16 mm |
| Car | ++++ | ++++ | ++++ | ++++ | ++ | + | 30 mm |
| Tyl | — | — | — | — | — | — | 30 mm |
| Ery | ++++ | ++ | + | + | + | + | 11 mm |

| Strain | Uninduced picA S. gris | | | | | |
|---|---|---|---|---|---|---|
| μg Conc, μg/ml Antibiotic | 10 | 50 | 100 | 250 | 500 | 1000 |
| Pc | ND | ND | ND | ND | ND | ND |
| Ros | ++++ | ++++ | ++++ | ++++ | ND | ND |
| Linc | ++++ | ++++ | ++++ | ++++ | ++++ | ++++ |
| Spi | ++++ | ++++ | ++ | ++ | + | — |
| Car | — | — | — | — | — | — |
| Tyl | ++++ | +++ | — | — | — | — |
| Ery | ++++ | ++++ | ++++ | ++++ | ++++ | +++ |

| Strain | Induced picA S. gris | | | | | |
|---|---|---|---|---|---|---|
| μg Conc, μg/ml Antibiotic | 10 | 50 | 100 | 250 | 500 | 1000 |
| Pc | ND | ND | ND | ND | ND | ND |
| Ros | ++++ | ++++ | ++++ | ++++ | ND | ND |
| Linc | ++++ | ++++ | ++++ | ++++ | ++++ | ++++ |
| Spi | ++++ | ++++ | ++++ | ++++ | +++ | + |
| Car | ++++ | — | — | — | — | — |
| Tyl | ++++ | ++++ | ++++ | ++++ | ++++ | — |
| Ery | ++++ | ++++ | ++++ | ++++ | ++++ | +++ | mm = zone size when plating 20 μg of antibiotic onto specified strain on TS agar plates. Plasmids were maintained under selection with Am25.
++++/strong growth +++/good growth ++/moderate growth +/weak growth —/no growth

I claim:

1. A recombinant DNA cloning vector which comprises
   a) a DNA sequence selected from the group consisting of an origin of replication and integration sequence, and
   b) a picromycin resistance gene, encoded on plasmid pOJ 321 that confers resistance to the antibiotic picromycin, and other macrolides,
subject to the limitation that said origin of replication and integration sequence are functional in Streptomyces and Nocardia.

2. The vector of claim 1 which is a plasmid.

3. A plasmid of claim 2 selected from the group consisting of plasmids pFJ372 and pFJ373.

4. The plasmid of claim 3 that is plasmid pFJ372.

5. The plasmid of claim 3 that is plasmid pFJ373.

6. A plasmid of claim 2 which is capable of integrating into the genome of Streptomyces.

7. A plasmid of claim 6 selected from the group consisting of plasmids pFJ374 and pFJ375.

8. The plasmid of claim 7 that is plasmid pFJ374.

9. The plasmid of claim 7 that is plasmid pFJ375.

10. The vector of claim 1 that is a phage.

11. A phage of claim 10 that is selected from the group consisting of phages pFJ376 and pFJ377.

12. The phage of claim 11 that is pFJ376.

13. The phage of claim 13 that is pFJ377.

14. The recombinant DNA cloning vector of claim 1 which further comprises
   a) an Escherichia coli origin of replication, and
   b) a DNA sequence that confers a suitable phenotype in Escherichia coli.

15. The vector of claim 14 that is a plasmid.

16. A plasmid of claim 15 that is selected from the group consisting of plasmids pOJ321, pFJ370 and pFJ371.

17. The plasmid of claim 16 that is plasmid pOJ321.

18. The plasmid of claim 16 that is plasmid pFJ370.

19. The plasmid of claim 18 that is plasmid pFJ371.

20. A constructed recombinant DNA sequence comprising the picromycin resistance gene of Streptomyces felleus encoded on plasmid pOJ321.

21. The ~2.8 kb PvuII restriction fragment of plasmid pOJ321.

22. A host cell transformed with a recombinant DNA cloning vector of claim 1.

23. A host cell transformed with a plasmid of claim 2.

24. A host cell transformed with a plasmid of claim 6.

25. A host cell transfected with a phage of claim 10.

26. A host cell transformed with a recombinant DNA cloning vector of claim 14.

27. A host cell transformed with a plasmid of claim 15.

28. A host cell of claim 27 that is selected from the group consisting of Streptomyces, Nocardia and Escherichia coli.

29. The transformed host cell of claim 28 which is Streptomyces.

30. The transformed host cell of claim 28 which is Nocardia.

31. The transformed host cell of claim 28 which is Escherichia-coli.

* * * * *